US008825135B2

(12) United States Patent
Okada

(10) Patent No.: US 8,825,135 B2
(45) Date of Patent: Sep. 2, 2014

(54) RADIOGRAPHIC IMAGE CAPTURING SYSTEM AND BIOPTIC METHOD USING RADIOGRAPHIC IMAGE CAPTURING SYSTEM

(75) Inventor: Naoyuki Okada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 40 days.

(21) Appl. No.: 13/219,108

(22) Filed: Aug. 26, 2011

(65) Prior Publication Data

US 2012/0053455 A1    Mar. 1, 2012

(30) Foreign Application Priority Data

Aug. 27, 2010   (JP) ................. 2010-191047

(51) Int. Cl.
| | | |
|---|---|---|
| *A61B 5/00* | (2006.01) | |
| *A61B 6/00* | (2006.01) | |
| *A61B 6/12* | (2006.01) | |
| *A61B 19/00* | (2006.01) | |
| *A61B 10/00* | (2006.01) | |
| *A61B 6/02* | (2006.01) | |
| *A61B 10/02* | (2006.01) | |
| *A61B 17/00* | (2006.01) | |

(52) U.S. Cl.
CPC ............. *A61B 6/022* (2013.01); *A61B 6/502* (2013.01); *A61B 2019/5238* (2013.01); *A61B 2019/507* (2013.01); *A61B 2019/5466* (2013.01); *A61B 10/0041* (2013.01); *A61B 6/025* (2013.01); *A61B 10/0275* (2013.01); *A61B 6/463* (2013.01); *A61B 19/5244* (2013.01); *A61B 6/12* (2013.01); *A61B 19/201* (2013.01); *A61B 2017/00455* (2013.01); *A61B 6/465* (2013.01); *A61B 6/00* (2013.01); *A61B 2019/205* (2013.01); *A61B 6/547* (2013.01)
USPC ............ 600/424; 600/407; 600/425; 600/427

(58) Field of Classification Search
USPC .................. 600/407, 424, 425, 427
See application file for complete search history.

(56) References Cited

U.S. PATENT DOCUMENTS 6,487,431 B1  11/2002  Iwano et al.
6,741,883 B2   5/2004  Gildenberg
(Continued)

FOREIGN PATENT DOCUMENTS

JP      07194616 A    8/1995
JP      10248793 A    9/1998
(Continued)

OTHER PUBLICATIONS

Notification of First Office Action, dated Apr. 2, 2014, issued in corresponding CN Application No. 201110251336.1, 13 pages in English and Chinese.

(Continued)

*Primary Examiner* — Peter Luong
(74) *Attorney, Agent, or Firm* — Sughrue Mion, PLLC

(57) ABSTRACT

A mammographic system which carries out a bioptic method for inserting a bioptic needle into a breast to sample a tissue from a bioptic region includes a display unit for displaying second stereoscopic images acquired by applying a radiation to the breast while the bioptic needle is being inserted in the breast, an indicating unit for indicating a pointed end of the bioptic needle and the bioptic region in each of the second stereoscopic images, a bioptic needle position calculator for calculating a three-dimensional coordinate position of the pointed end of the bioptic needle which is indicated, a bioptic region position calculator for calculating a three-dimensional coordinate position of the bioptic region which is indicated, and an angle calculator for calculating a direction of the calculated bioptic region with respect to the calculated pointed end of the bioptic needle and displaying the calculated direction on the display unit.

8 Claims, 14 Drawing Sheets

(56) References Cited

U.S. PATENT DOCUMENTS

| | | |
|---|---|---|
| 2008/0045833 A1 | 2/2008 | Defreitas et al. |
| 2010/0113970 A1 | 5/2010 | Okada |

FOREIGN PATENT DOCUMENTS

| | | |
|---|---|---|
| JP | 2000-175897 A | 6/2000 |
| JP | 2000197630 A | 7/2000 |
| JP | 2005-518854 A | 6/2005 |
| JP | 2009-526618 A | 7/2009 |
| JP | 2010-075316 A | 4/2010 |
| JP | 2010-075317 A | 4/2010 |
| JP | 2010-110418 A | 5/2010 |
| JP | 2010137004 A | 6/2010 |

OTHER PUBLICATIONS

Rejection of the Application, dispatched Dec. 17, 2013, issued in corresponding JP Application No. 2010-191047, 5 pages in English and Japanese.

10

RADIOGRAPHIC IMAGE CAPTURING SYSTEM AND BIOPTIC METHOD USING RADIOGRAPHIC IMAGE CAPTURING SYSTEM

CROSS-REFERENCE TO RELATED APPLICATION

This application is based upon and claims the benefit of priority from Japanese Patent Application No. 2010-191047 filed on Aug. 27, 2010, of which the contents are incorporated herein by reference.

BACKGROUND OF THE INVENTION

1. Field of the Invention

The present invention relates to a radiographic image capturing system which applies a radiation to an object to be examined thereby to acquire a stereoscopic image of the object, and a bioptic method which uses such a radiographic image capturing system.

2. Description of the Related Art

Heretofore, there has widely been carried out a bioptic method which uses a radiographic image capturing system. The bioptic method comprises applying a radiation to an object to be examined thereby to acquire a stereoscopic image of the object, calculating a three-dimensional coordinate position of a bioptic region (e.g., a lesion in a breast) in the object from the stereoscopic image, inserting a bioptic needle into the object based on the calculated three-dimensional coordinate position, and sampling a tissue of the bioptic region in the object under suction with a sampler (opening) of the bioptic needle (for details, see Japanese Laid-Open Patent Publication No. 2010-110418, Japanese Laid-Open Patent Publication No. 2010-075316, and Japanese Laid-Open Patent Publication 2010-075317).

In order to sample a tissue of the bioptic region in the bioptic method, it is necessary to recognize the exact positional relationship between the bioptic needle as inserted into the object to be examined and the bioptic region, and place the opening of the bioptic needle in the vicinity of the bioptic region (e.g., at a position facing the bioptic region) based on the recognized positional relationship.

According to a known process of recognizing the above positional relationship, while the bioptic needle is being inserted in the object to be examined, a radiation is applied to the object to acquire a tomosynthetic image thereof, and the position of the bioptic needle with respect to the bioptic region (area to be examined) is specified from the tomosynthetic image (for details, see Japanese Laid-Open Patent Publication No. 2009-526618).

In connection with brain tumor surgery and surgery with catheterization, there is known a process of generating a three-dimensional image of the patient using a CT (Computerized Tomography) apparatus and displaying the tip end of a probe (catheter) in the three-dimensional image in order to recognize the exact position of the probe in the patient (for details, see Japanese Laid-Open Patent Publication No. 2005-518854 and Japanese Laid-Open Patent Publication No. 2000-175897).

In the process disclosed in Japanese Laid-Open Patent Publication No. 2009-526618, the positional relationship between the bioptic needle and the bioptic region in the tomosynthetic image is different from an actual positional relationship in a three-dimensional coordinate system. Therefore, the radiological technician or doctor (hereinafter referred to as "technician or the like") who is in charge needs to interpret the tomosynthetic image and determine the positional relationship between the bioptic needle and the bioptic region in the three-dimensional coordinate system from the tomosynthetic image. The positional relationship thus determined may vary in its accuracy depending on the experience of the technician or the like. As a result, a tissue of the bioptic region may not be reliably sampled.

According to the process disclosed in Japanese Laid-Open Patent Publication No. 2005-518854 and Japanese Laid-Open Patent Publication No. 2000-175897, the process of generating a three-dimensional image is liable to require a complex processing sequence and a complex control system.

SUMMARY OF THE INVENTION

It is an object of the present invention to provide a radiographic image capturing system which is capable of sampling a tissue of a bioptic region in an object to be examined easily and reliably with a bioptic needle, and a bioptic method which uses such a radiographic image capturing system.

According to the present invention, there is provided a radiographic image capturing system for inserting a bioptic needle into an object to be examined and sampling a tissue from a bioptic region of the object through an opening of the bioptic needle, comprising display means for displaying stereoscopic images acquired by applying a radiation to the object while the bioptic needle is being inserted in the object, indicating means for indicating a feature point of the bioptic needle and the bioptic region in each of the stereoscopic images displayed by the display means, bioptic needle position calculating means for calculating a three-dimensional coordinate position of the feature point of the bioptic needle indicated by the indicating means, bioptic region position calculating means for calculating a three-dimensional coordinate position of the bioptic region indicated by the indicating means, direction calculating means for calculating a direction of the three-dimensional coordinate position of the bioptic region with respect to the three-dimensional coordinate position of the feature point of the bioptic needle, and announcing means for announcing the direction calculated by the direction calculating means.

With the above radiographic image capturing system, the direction calculating means calculates a direction of the three-dimensional coordinate position of the bioptic region with respect to the three-dimensional coordinate position of the feature point of the bioptic needle, and the announcing means announces the direction calculated by the direction calculating means. Therefore, the technician or the like can adjust the position of the opening of the bioptic needle based on the calculated direction, for thereby bringing the opening into a position which faces the bioptic region. Consequently, a tissue of the bioptic region can reliably be sampled by the bioptic needle. According to the radiographic image capturing system, the calculating process is not complex because there is no need to generate a three-dimensional image.

The radiographic image capturing system should preferably further comprise distance calculating means for calculating a distance represented by the length of a line segment which interconnects the three-dimensional coordinate position of the feature point of the bioptic needle and the three-dimensional coordinate position of the bioptic region, as projected onto a plane lying perpendicularly to an inserting direction along which the bioptic needle is inserted in the object, and the announcing means should preferably announce the distance calculated by the distance calculating means.

Since the distance calculating means calculates a distance represented by the length of a line segment which interconnects the three-dimensional coordinate position of the feature point of the bioptic needle and the three-dimensional coordinate position of the bioptic region, as projected onto a plane lying perpendicularly to an inserting direction along which the bioptic needle is inserted in the object, and the announcing means announces the distance calculated by the distance calculating means, the technician or the like can finely adjust the position of the bioptic region by pressing the object in a direction perpendicular to the inserting direction of the bioptic needle based on the calculated distance, for example. Consequently, the bioptic region can be placed in an appropriate position with respect to the bioptic needle, and hence a tissue can be sampled from the bioptic region reliably by the bioptic needle.

The radiographic image capturing system should preferably further comprise decision means for determining whether the three-dimensional coordinate position of the bioptic region is within an opening range of the opening of the bioptic needle or not, and the announcing means should preferably announce the decision made by the decision means if the decision means judges that the three-dimensional coordinate position of the bioptic region falls outside of the opening range.

If the three-dimensional coordinate position of the bioptic region falls outside of the opening range of the opening of the bioptic needle in the inserting direction of the bioptic needle, then the object may be pressed in the inserting direction of the bioptic needle to finely adjust the position of the bioptic region to position the three-dimensional coordinate position of the bioptic region in the opening range. Therefore, a tissue can be sampled from the bioptic region reliably by the bioptic needle.

The radiographic image capturing system should preferably further comprise opening position calculating means for calculating a position of the opening of the bioptic needle based on the three-dimensional coordinate position of the feature point of the bioptic needle.

As the positional relationship between the three-dimensional coordinate position of the bioptic region and the opening of the bioptic needle becomes clear, it is easy to determine whether the three-dimensional coordinate position of the bioptic region is within the opening range of the opening of the bioptic needle in the inserting direction of the bioptic needle or not.

The radiographic image capturing system should preferably further comprise input means for inputting the inserting direction along which the bioptic needle is inserted in the object, and the opening position calculating means should preferably calculate the position of the opening of the bioptic needle based on the inserting direction inputted by the input means.

The position of the opening of the bioptic needle can reliably be calculated even if a plurality of inserting directions of the bioptic needle can be set with respect to the object to be examined.

The display means should preferably function as the announcing means by displaying the direction calculated by the direction calculating means, the distance calculated by the distance calculating means, and the decision made by the decision means.

The radiographic image capturing system is thus made up of a smaller number of parts than if an announcing means is provided separately from the display means.

The radiographic image capturing system should preferably further comprise mode selecting means for selecting a bioptic needle indicating mode for indicating the feature point of the bioptic needle in each of the stereoscopic images and a bioptic region indicating mode for indicating the bioptic region in each of the stereoscopic images.

The technician or the like can freely select the bioptic region indicating mode or the bioptic needle indicating mode from the mode setting section. Therefore, the technician or the like can efficiently and accurately indicate the bioptic region and the bioptic needle.

The bioptic needle should preferably be of a tapered shape including a pointed end, and the pointed end should preferably serve as the feature point of the bioptic needle in each of the stereoscopic images. Since the feature point of the bioptic needle is specified as one point, the feature point of the bioptic needle can accurately be indicated in each of the stereoscopic images.

The opening of the bioptic needle should preferably be constructed so as to be displayed as being substantially U-shaped in each of the stereoscopic images, and the feature point of the bioptic needle should preferably be positioned on an opening forming line which defines the opening of the bioptic needle in each of the stereoscopic images. Therefore, the bioptic needle position calculating means can easily calculate the three-dimensional coordinate position of the opening of the bioptic needle.

The feature point of the bioptic needle should preferably be positioned on either one of a pair of opposite sides, which face each other, of the opening forming line.

Therefore, the bioptic needle position calculating means can easily calculate the three-dimensional coordinate position of the opening of the bioptic needle, and the feature point of the bioptic needle is indicated with increased accuracy in each of the stereoscopic images.

The feature point of the bioptic needle should preferably comprise a point positioned substantially centrally on a side interconnecting a pair of opposite sides, which face each other, of the opening forming line.

Therefore, the bioptic needle position calculating means can easily calculate the three-dimensional coordinate position of the opening of the bioptic needle, and the feature point of the bioptic needle is indicated with increased accuracy in each of the stereoscopic images.

According to the present invention, there is also provided a bioptic method inserting a bioptic needle into an object to be examined and sampling a tissue from a bioptic region of the object through an opening of the bioptic needle, comprising the displaying step of displaying stereoscopic images acquired by applying a radiation to the object while the bioptic needle is being inserted in the object, the first indicating step of indicating, with indicating means, a feature point of the bioptic needle in each of the stereoscopic images displayed by the display means, the second indicating step of indicating, with the indicating means, a bioptic region in each of the stereoscopic images displayed by the display means, the bioptic needle position calculating step of calculating a three-dimensional coordinate position of the feature point of the bioptic needle indicated by the indicating means, the bioptic region position calculating step of calculating a three-dimensional coordinate position of the bioptic region indicated by the indicating means, the direction calculating step of calculating a direction of the three-dimensional coordinate position of the bioptic region calculated in the bioptic region position calculating step with respect to the three-dimensional coordinate position of the feature point of the bioptic needle, and the announcing step of announcing the direction calculated in the direction calculating step.

With the above bioptic method, the technician or the like can adjust the position of the opening of the bioptic needle based on the direction calculated in the direction calculating step, for thereby bringing the opening into a position which faces the bioptic region. Consequently, a tissue of the bioptic region can reliably be sampled by the bioptic needle. According to the bioptic method, the calculating process is not complex because there is no need to generate a three-dimensional image.

According to the present invention, as described above, since the technician or the like can adjust the position of the opening of the bioptic needle based on the direction calculated by the direction calculating means or in the direction calculating step, for thereby bringing the opening into a position which faces the bioptic region, a tissue of the bioptic region can reliably be sampled by the bioptic needle. The calculating process is not complex because the radiographic image capturing system does not need to generate a three-dimensional image.

The above and other objects, feature points, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

A bioptic method for sampling a tissue of a bioptic region of an object to be examined according to a preferred embodiment of the present invention, in relation to a radiographic image capturing system which carries out the bioptic method, will be described below with reference to the accompanying drawings.

Figure 1:
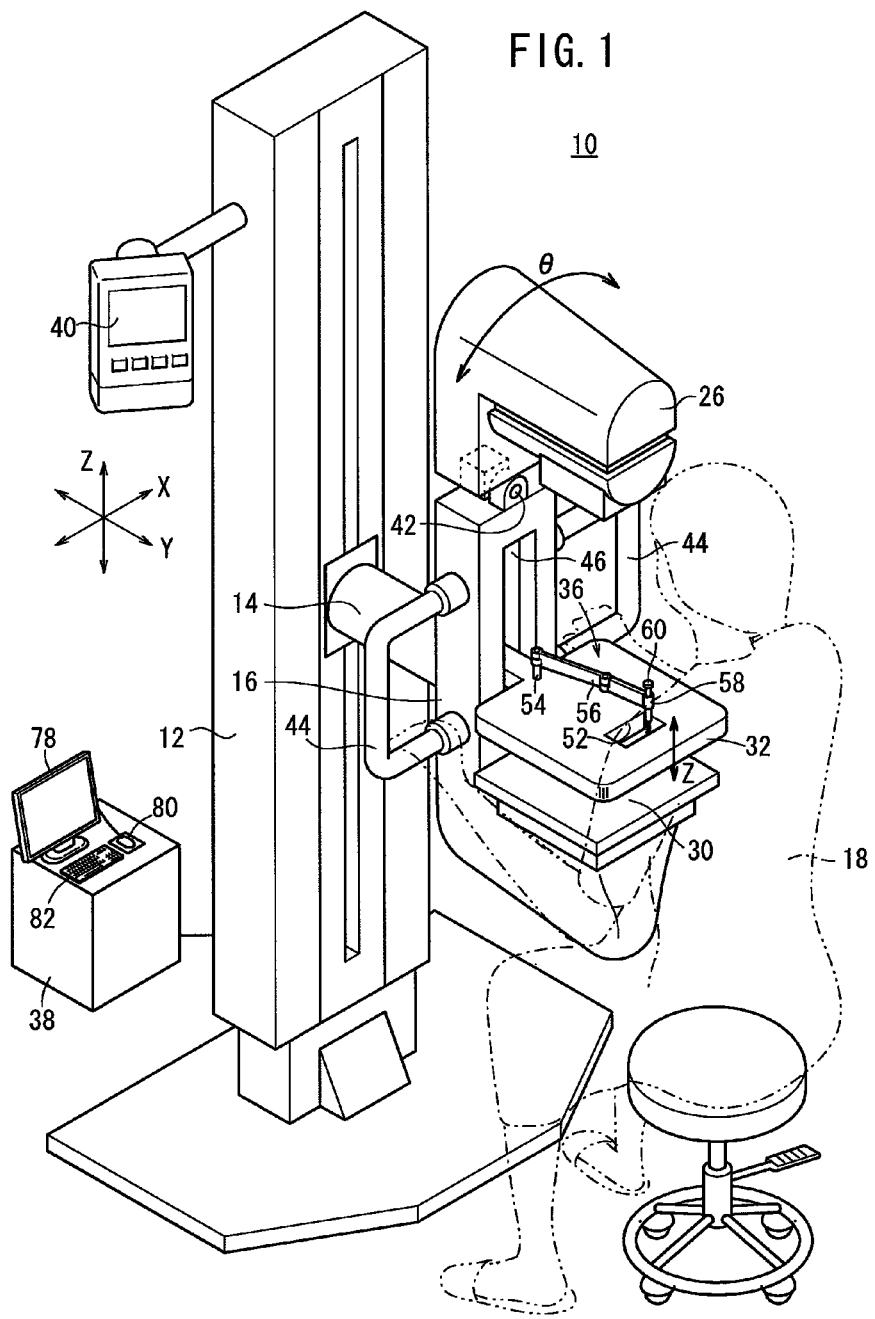
FIG. 1 is a perspective view of a mammographic system as a radiographic image capturing system according to an embodiment of the present invention.
Figure 2:
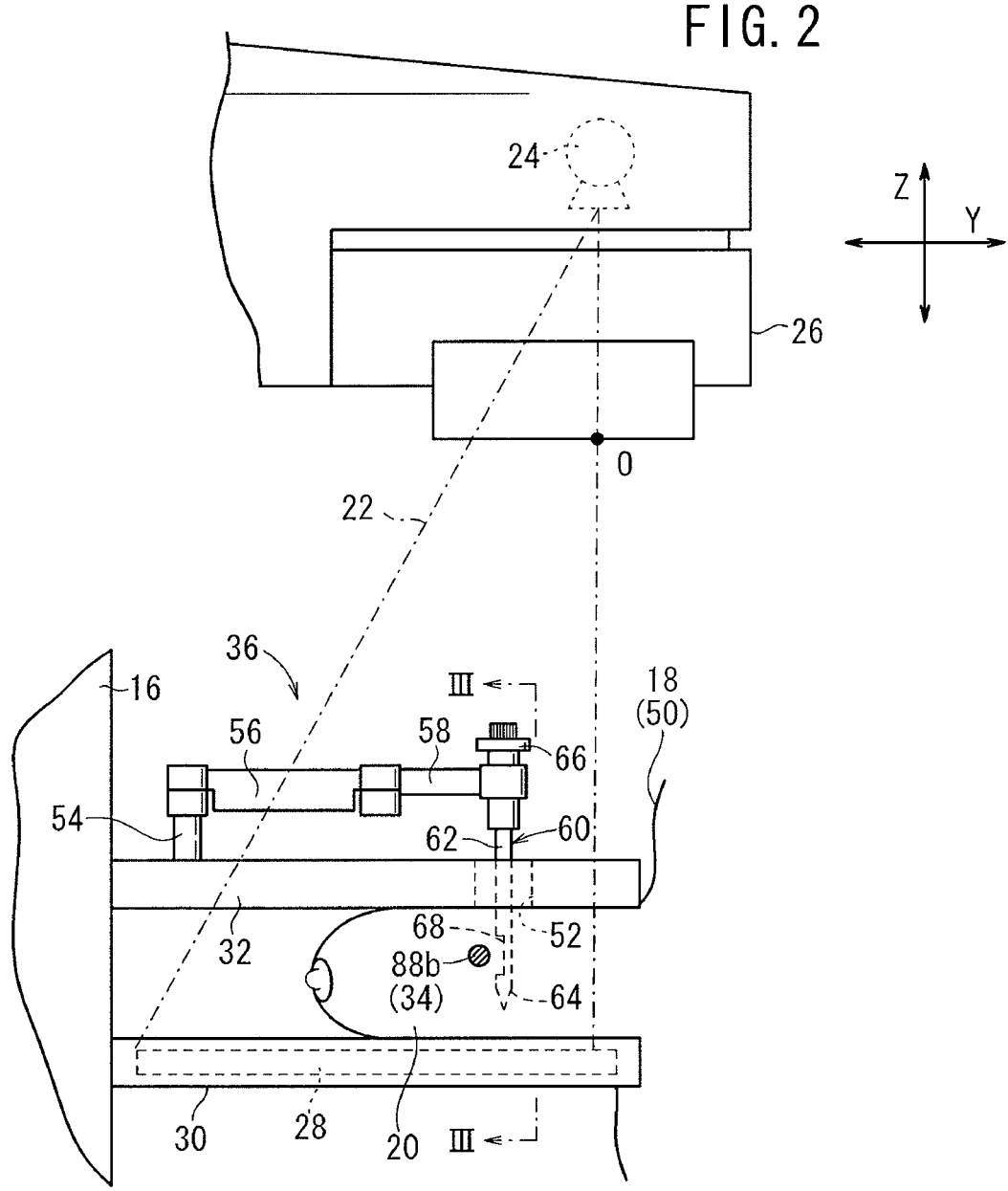
FIG. 2 is an enlarged fragmentary side elevational view of the mammographic system shown in FIG. 1.

As shown in FIGS. 1 and 2, a mammographic system 10 as the radiographic image capturing system basically includes an upstanding base 12, a vertical arm 16 fixed to the distal end of a swing shaft 14 disposed substantially centrally on the base 12, a radiation source housing unit 26 housing therein a radiation source 24 for applying a radiation 22 to a breast 20 as an object to be examined of an examinee (subject) 18 and fixed to an upper end of the arm 16, an image capturing base 30 mounted on the lower end of the arm 16 and housing therein a solid-state detector (radiation detector) 28 for detecting the radiation 22 which has passed through the breast 20, a compression plate 32 for compressing and holding the breast 20 against the image capturing base 30, a bioptic hand assembly 36 for sampling a tissue from a bioptic region 34 of the breast 20, the bioptic hand assembly 36 being mounted on the compression plate 32, and a console 38 electrically connected to the base 12 through a wired link. The expression "disposed substantially centrally" used above means that the vertical arm 16 is disposed at a position in an area including the center and its vicinity of the base 12.

In FIG. 1, the mammographic system 10 applies the radiation 22 to the breast 20 of the examinee 18 and samples a tissue from the bioptic region 34 while the breast 20 of the examinee 18 who is in a sitting position is being compressed and secured by the compression plate 32 and the image capturing base 30. To the base 12, there is connected a display control panel 40 for setting and displaying image capturing conditions representing an image capturing region, etc. of the examinee 18, the ID information of the examinee 18, etc.

When the arm 16, to which the radiation source housing unit 26 and the image capturing base 30 are secured, is angularly moved about the swing shaft 14, the direction of the radiation source housing unit 26 and the image capturing base 30 with respect to the breast 20 of the examinee 18 is adjusted. The radiation source housing unit 26 is operatively coupled to the arm 16 by a hinge 42 and can be turned about the hinge 42 in the directions indicated by the arrow θ independently of the image capturing base 30. Handles 44, which are to be gripped by the examinee 18, are mounted on the respective sides of the arm 16 which face away from each other along the directions indicated by the arrow X.

The compression plate 32 has a proximal end inserted in a groove 46 defined in the arm 16. The compression plate 32 is disposed between the radiation source housing unit 26 and the image capturing base 30. The compression plate 32 is vertically displaceable in the directions indicated by the arrow Z.

The bioptic hand assembly 36 is mounted on a surface of the compression plate 32 which faces the radiation source 24, in the vicinity of the groove 46. The compression plate 32 has an opening 52 defined therein near a chest wall 50 (see FIG. 2) of the examinee 18, for allowing the bioptic hand assembly 36 to remove a tissue sample from the bioptic region 34 of the breast 20.

The compression plate 32 may be detachable from the groove 46. A plurality of compression plates 32 with differently shaped openings 52 defined therein may be kept available for ready use, and one of the compression plates 32 whose opening 52 is best suited to the examinee 18 may be used to let the examinee 18 sit in a natural stress-free position while a biopsy is being performed on the examinee 18.

The bioptic hand assembly 36 comprises a post 54 fixedly mounted on the compression plate 32, a first arm 56 having an end pivotally supported on the post 54 and angularly movable about the post 54 along the surface of the compression plate 32, and a second arm 58 having an end pivotally supported on the other end of the first arm 56 and angularly movable about the other end of the first arm 56 along the surface of the compression plate 32.

Figure 3:
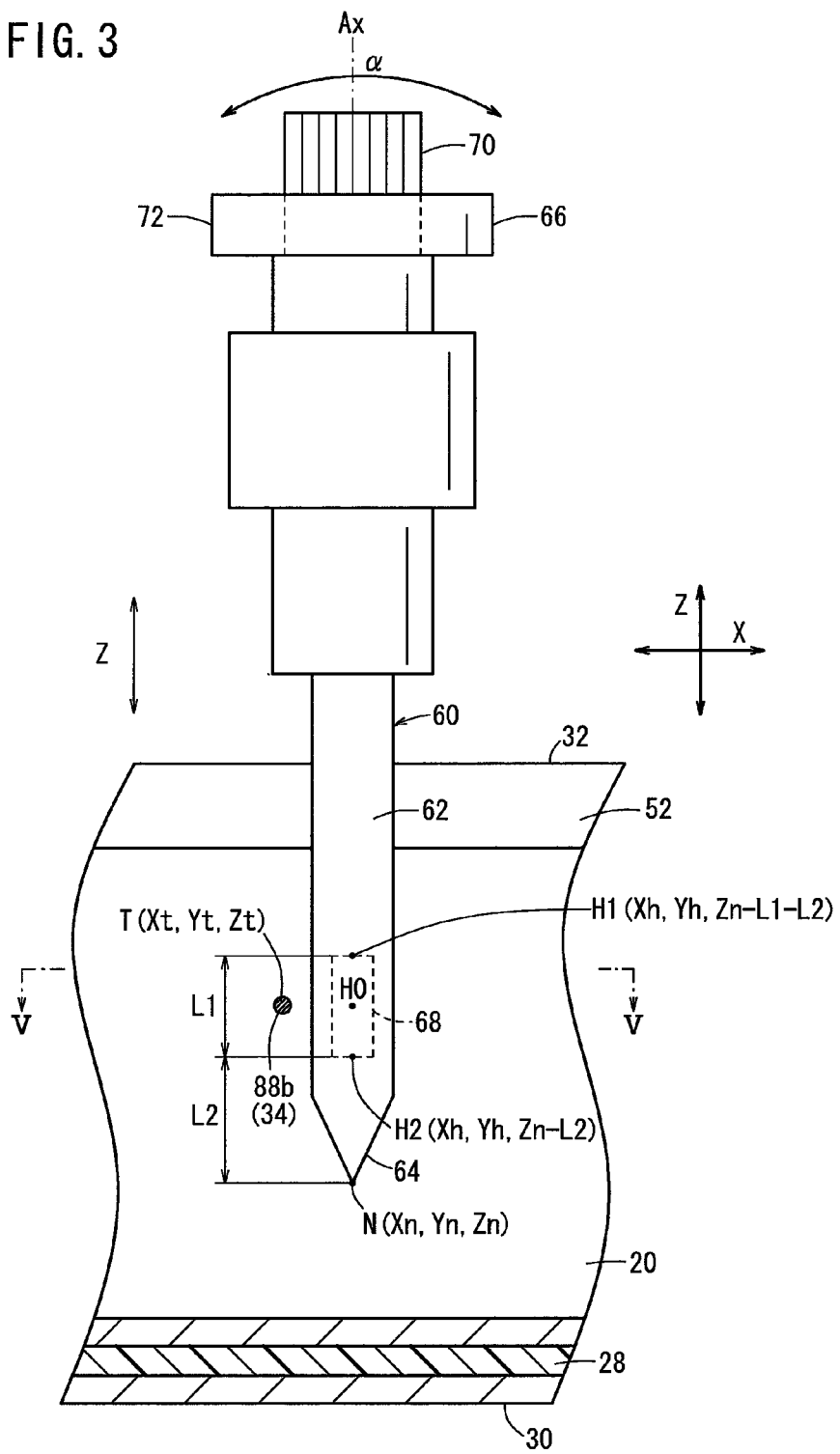
FIG. 3 is a cross-sectional view taken along line III-III of FIG. 2.

As shown in FIG. 3, a bioptic needle 60 which is tiltable in the directions indicated by the arrow α is movably mounted on the other end of the second arm 58. The bioptic needle 60 is movable along its own axis. Since the bioptic needle 60 is tiltable and axially movable, it can be inserted into the breast 20 along a plurality of different directions. In the present embodiment, it is assumed that the bioptic needle 60 is inserted into the breast 20 along a direction indicated by the arrow Z.

The bioptic needle 60 includes a hollow cylindrical main body 62 which is rotatable about its own axis Ax, a tapered portion 64 disposed on a distal end of the main body 62, and an opening position adjusting mechanism 66 disposed on a proximal end of the main body 62.

The main body 62 has an opening 68 defined in an outer circumferential wall thereof near its distal end for introducing a tissue (e.g., a calcified tissue) from the bioptic region 34 of the breast 20 into the main body 62 under suction from a suction device, not shown. The opening 68 is rectangular in shape as viewed in side elevation and is elongate in the directions indicated by the arrow Z. However, the opening 68 may be of any desired shape, e.g., a circular shape, an elliptical shape, or a polygonal shape as viewed in side elevation.

The opening 68 of the bioptic needle 60 can be moved to a position in the vicinity of the bioptic region 34 when the first arm 56 and the second arm 58 of the bioptic hand assembly 36 are moved in an X-Y plane parallel to the surface of the compression plate 32 and the bioptic needle 60 is moved in the directions indicated by the arrow Z.

The tapered portion 64 of the bioptic needle 60 has its pointed end N positioned on the axis Ax of the bioptic needle 60. Consequently, the pointed end N of the tapered portion 64 is prevented from being concealed by the main body 62 when the mammographic system 10 operates in a stereoscopic image capturing process to be described later. Alternatively, the pointed end N of the tapered portion 64 may be offset from the axis Ax of the bioptic needle 60.

The opening position adjusting mechanism 66 includes a dial 70 that is rotatable in unison with the main body 62, and an azimuth indicator 72 supported on the second arm 58 and extending around the dial 70.

Figure 4:
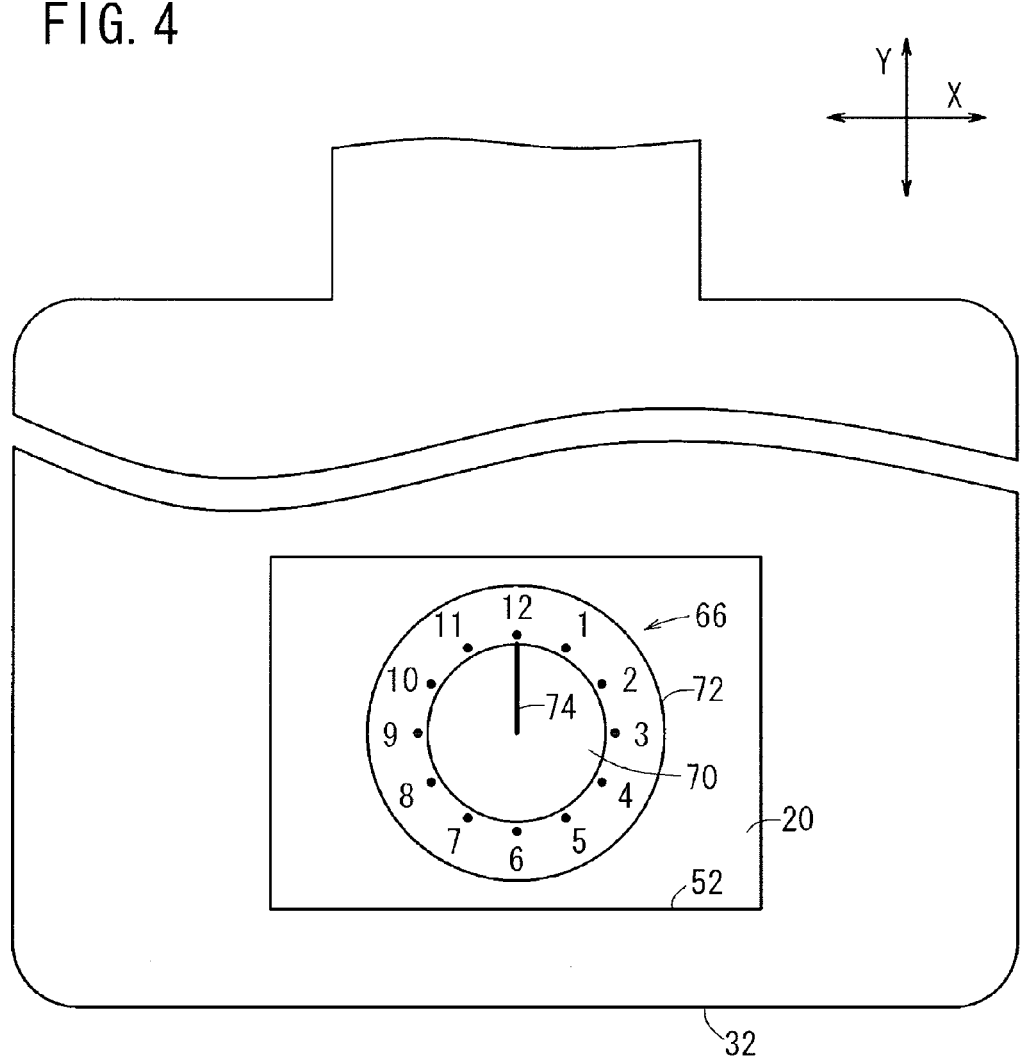
FIG. 4 is a plan view of a bioptic needle and a compression plate shown in FIG. 3.

As shown in FIG. 4, the dial 70 has a marker 74 on an end face thereof which faces in a direction indicated by the arrow Z. The marker 74 serves to indicate in an X-Y plane the direction of the opening 68 defined in the main body 62. The marker 74, which is linear in shape, is aligned with the center H0 of the opening 68 when it is projected in a direction indicated by the arrow Z (see FIG. 5).

Figure 5:
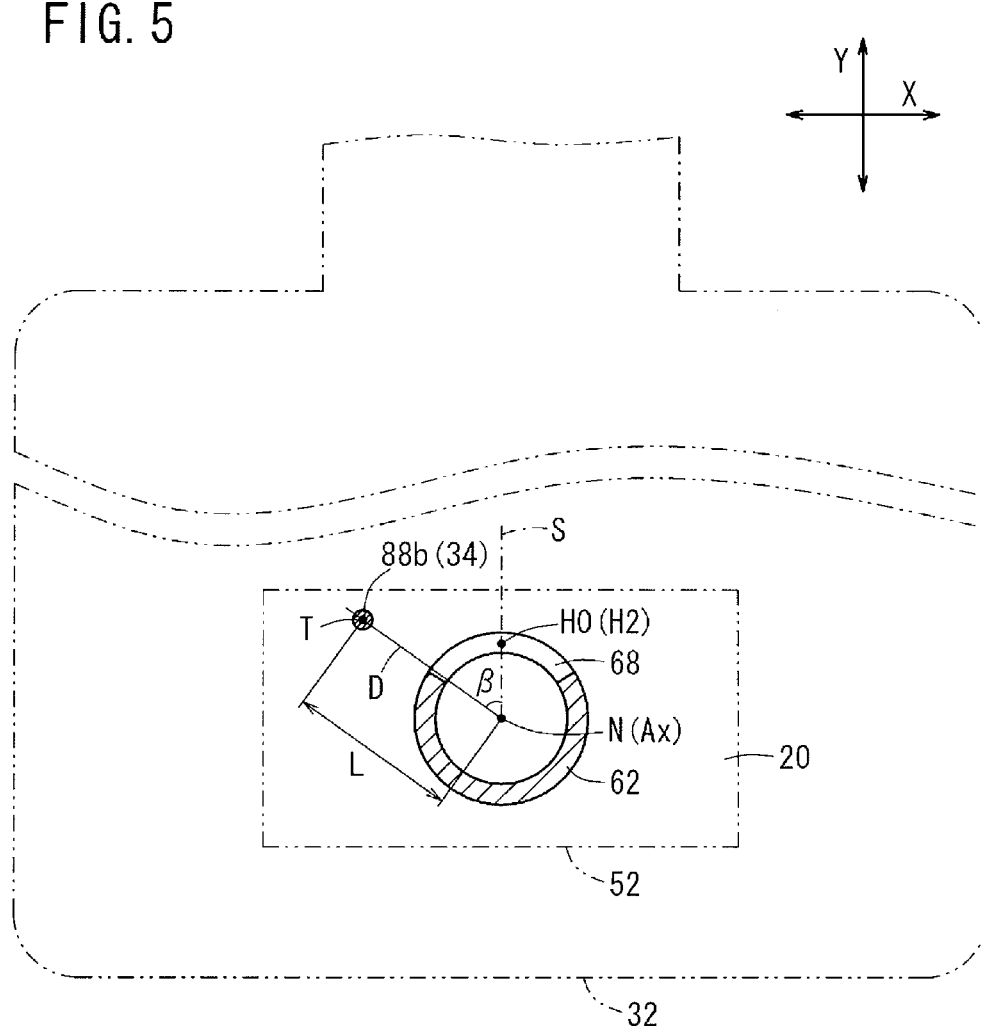
FIG. 5 is a cross-sectional view taken along line V-V of FIG. 3.

The azimuth indicator 72 has graduations on an end face thereof which faces in the direction indicated by the arrow Z. The graduations are spaced at angular intervals of 30 degrees around the dial 70, and associated with respective numerals from 1 through 12. In the present embodiment, the direction oriented from the axis of the bioptic needle 60 toward the base 12 is used as a 12 o'clock direction. The marker 74 and the graduations make it easy to recognize the direction in which the opening 68 faces when the bioptic needle 60 is inserted into the breast 20. In FIGS. 4 and 5, the marker 74 is positioned in the 12 o'clock direction, and hence the opening 68 is also open in the 12 o'clock direction. The azimuth indicator 72 may have any desired graduations and associated numerals other than those illustrated.

Figure 6:
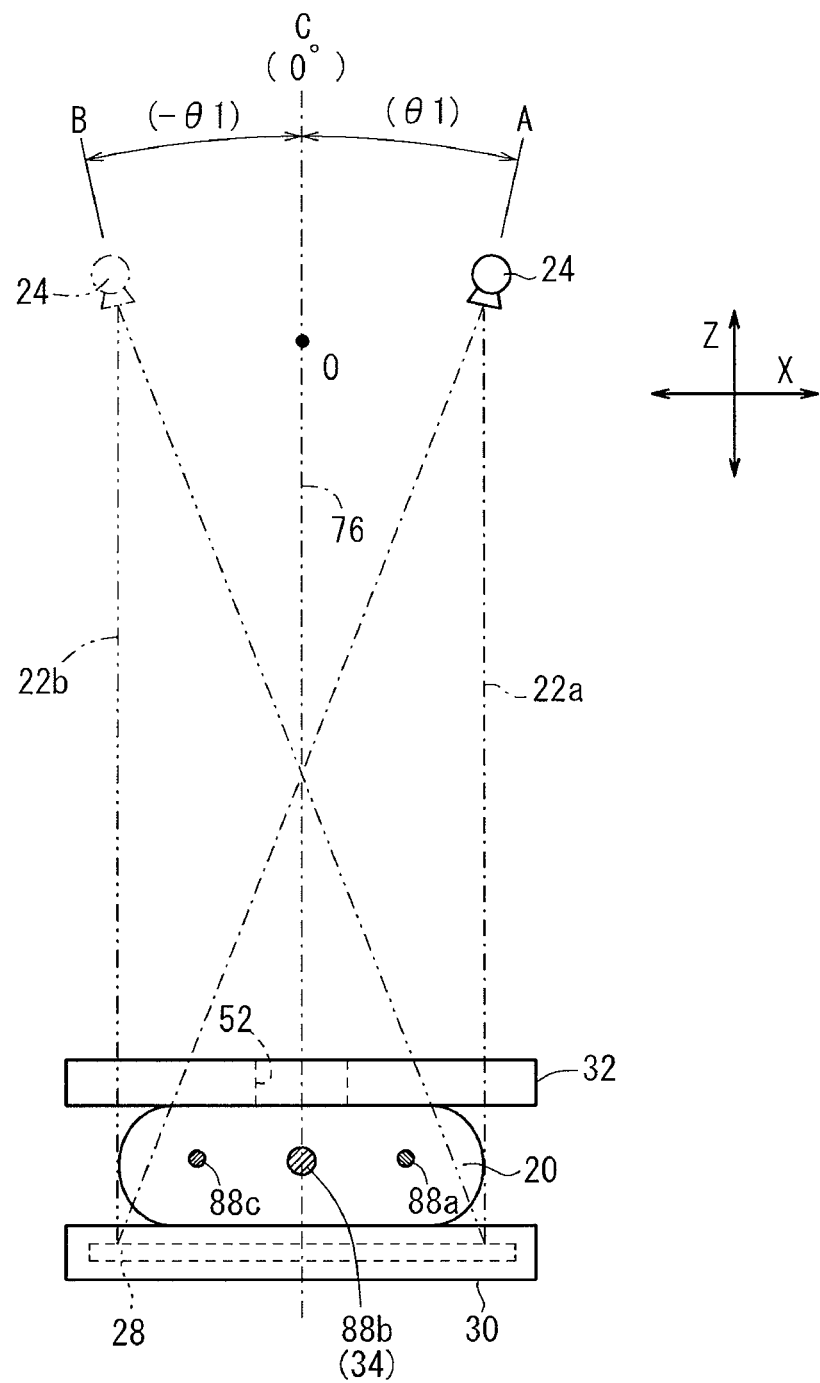
FIG. 6 is a schematic front elevational view illustrative of a stereoscopic image capturing process.

As shown in FIG. 6, when the mammographic system 10 operates in the stereoscopic image capturing process, the radiation source 24 which is disposed in positions A, B obliquely to the vertical axis (central axis) of the solid-state detector 28 applies radiations 22a, 22b from the respective positions A, B to the breast 20. The solid-state detector 28 detects the radiations 22a, 22b that have passed through the breast 20 and converts the detected radiations 22a, 22b into respective radiographic images in the stereoscopic image capturing process.

In the mammographic system 10, the number of stereoscopic images to be captured and the order in which they are to be captured are set as desired by the technician or the like. The radiation source 24 is angularly moved between the positions A, B when the radiation source housing unit 26 is turned about the hinge 42.

In the stereoscopic image capturing process according to the present embodiment, the radiation source 24 applies the radiations 22a, 22b from the respective positions A, B when the radiation source 24 is in the positions A, B. However, the mammographic system 10 may operate in another stereoscopic image capturing process in which the radiation source 24 applies radiations 22 from the position A and a position C on the central axis 76 when the radiation source 24 is in the positions A, C, or in still another stereoscopic image capturing process in which the radiation source 24 applies radiations 22 from the respective positions B, C when the radiation source 24 is in the positions B, C.

Figure 7:
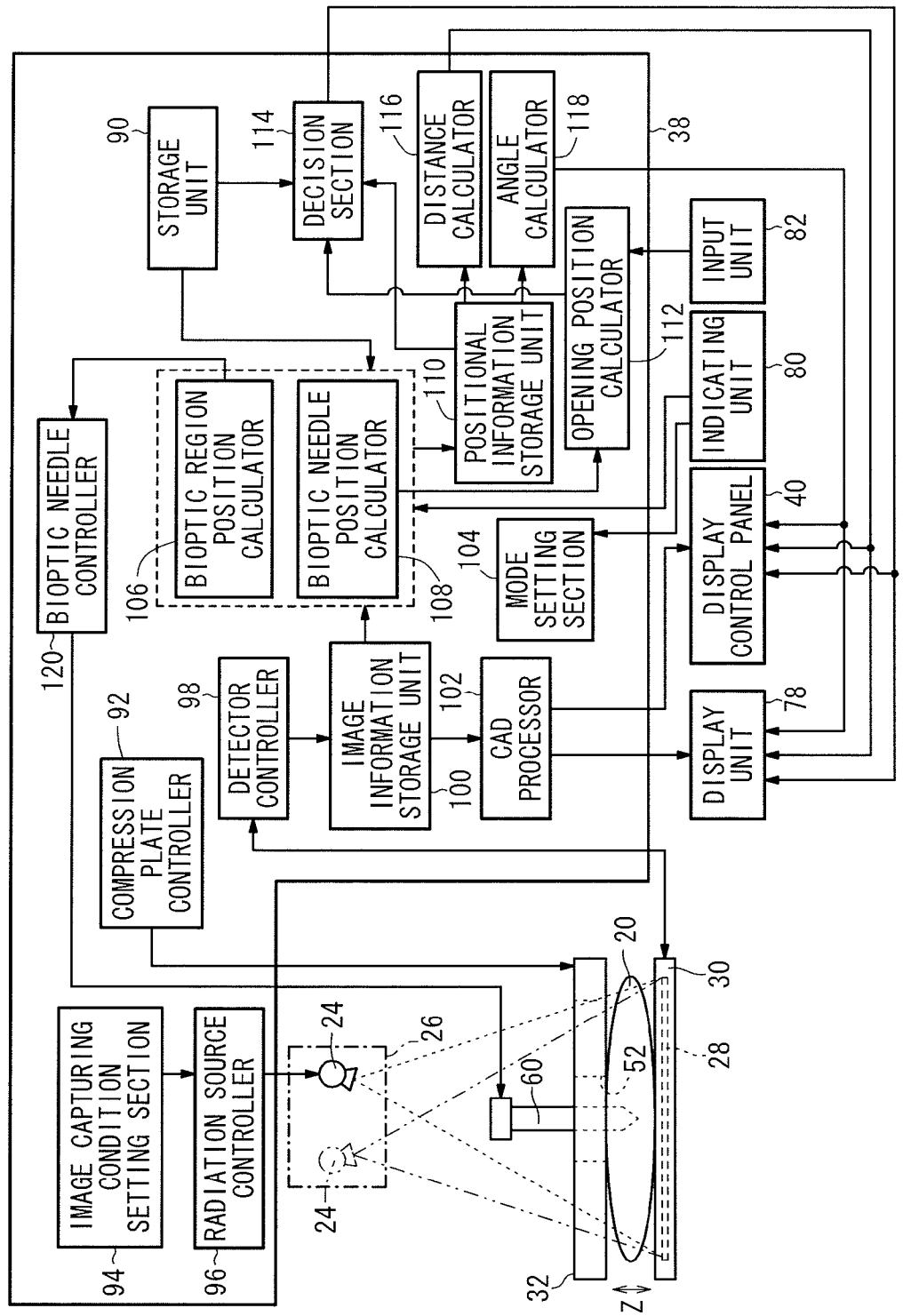
FIG. 7 is a block diagram of the mammographic system shown in FIG. 1.
Figure 10:
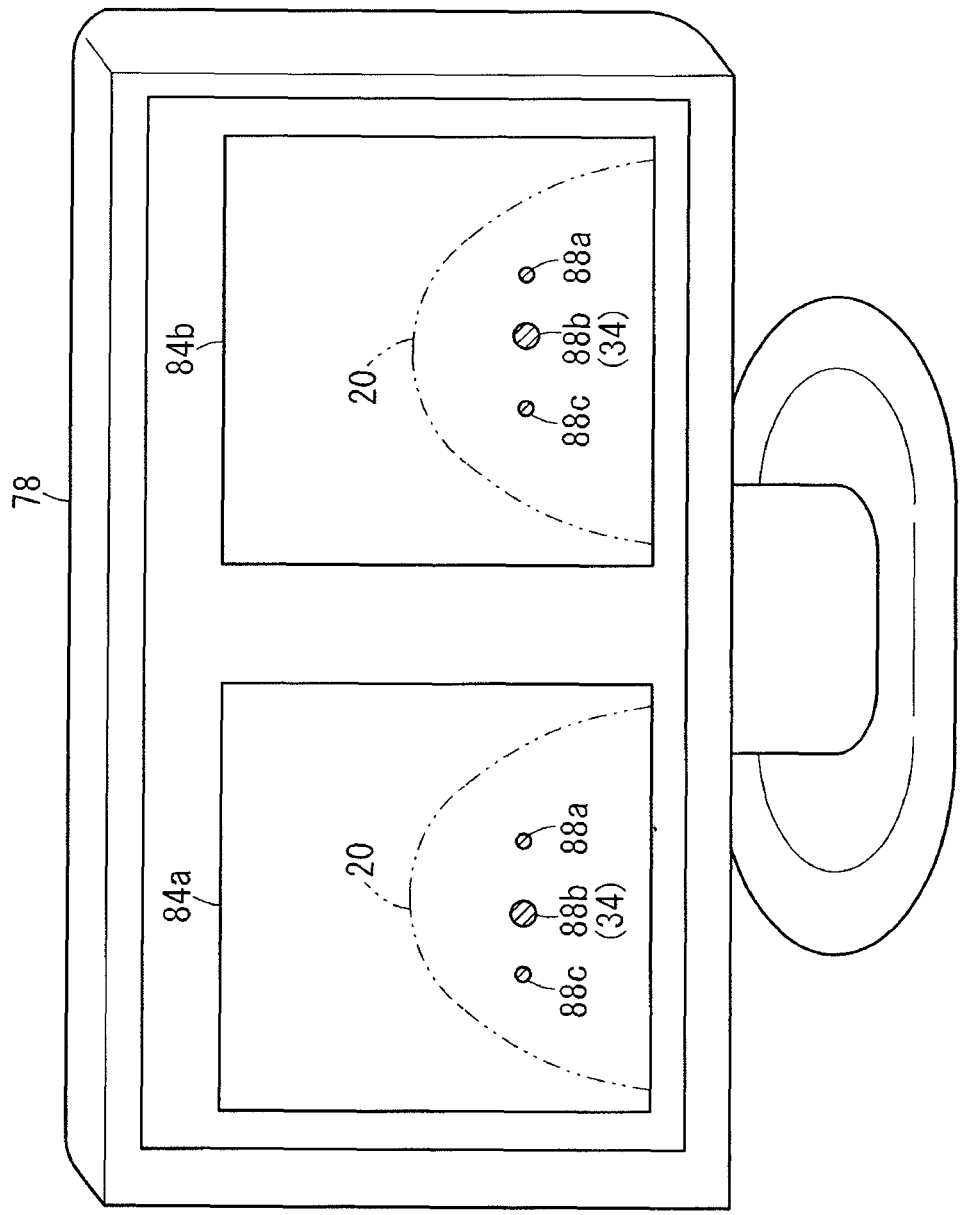
FIG. 10 is a perspective view of a display unit which is displaying first stereoscopic images.
Figure 11:
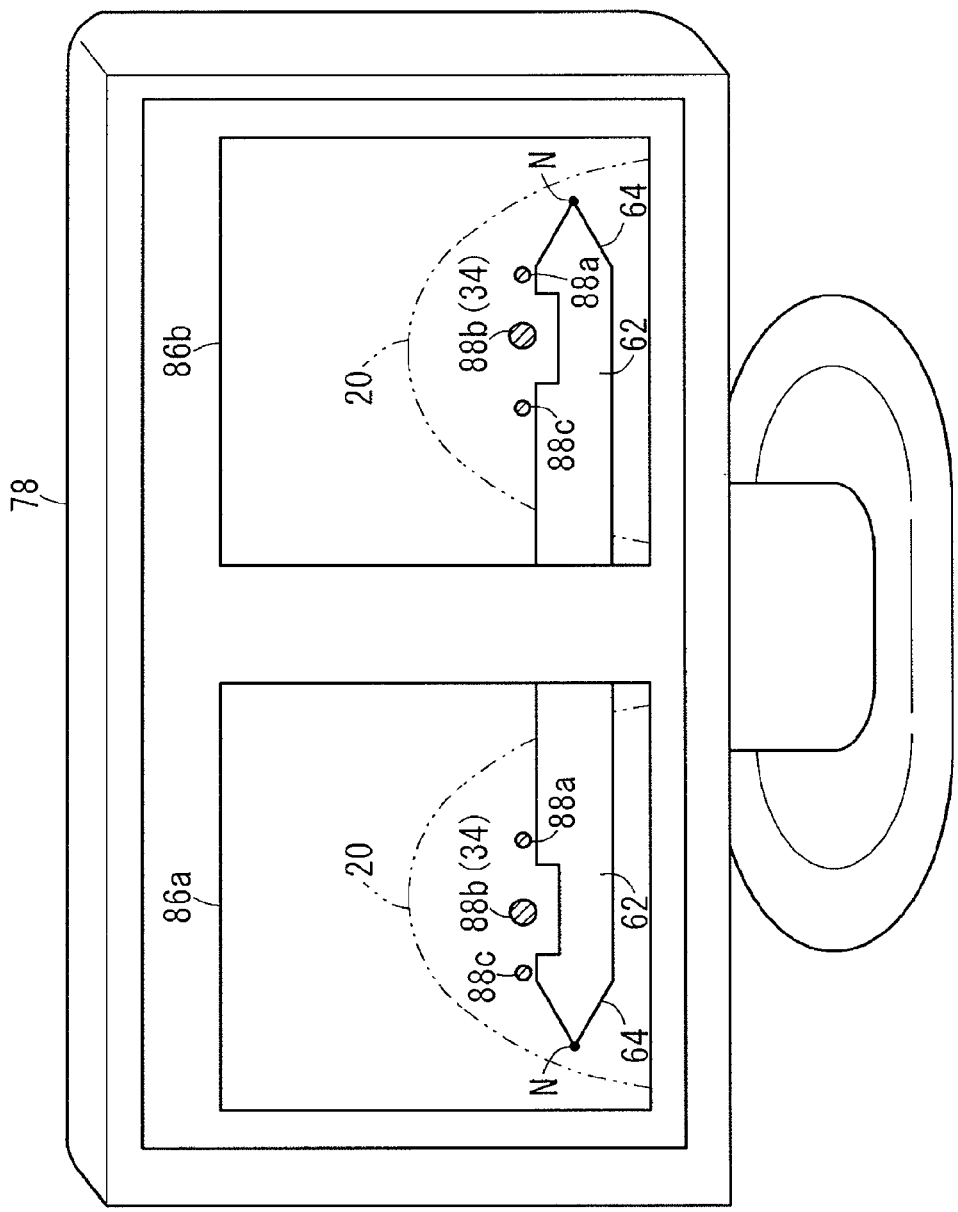
FIG. 11 is a perspective view of the display unit which is displaying second stereoscopic images.
Figure 12:
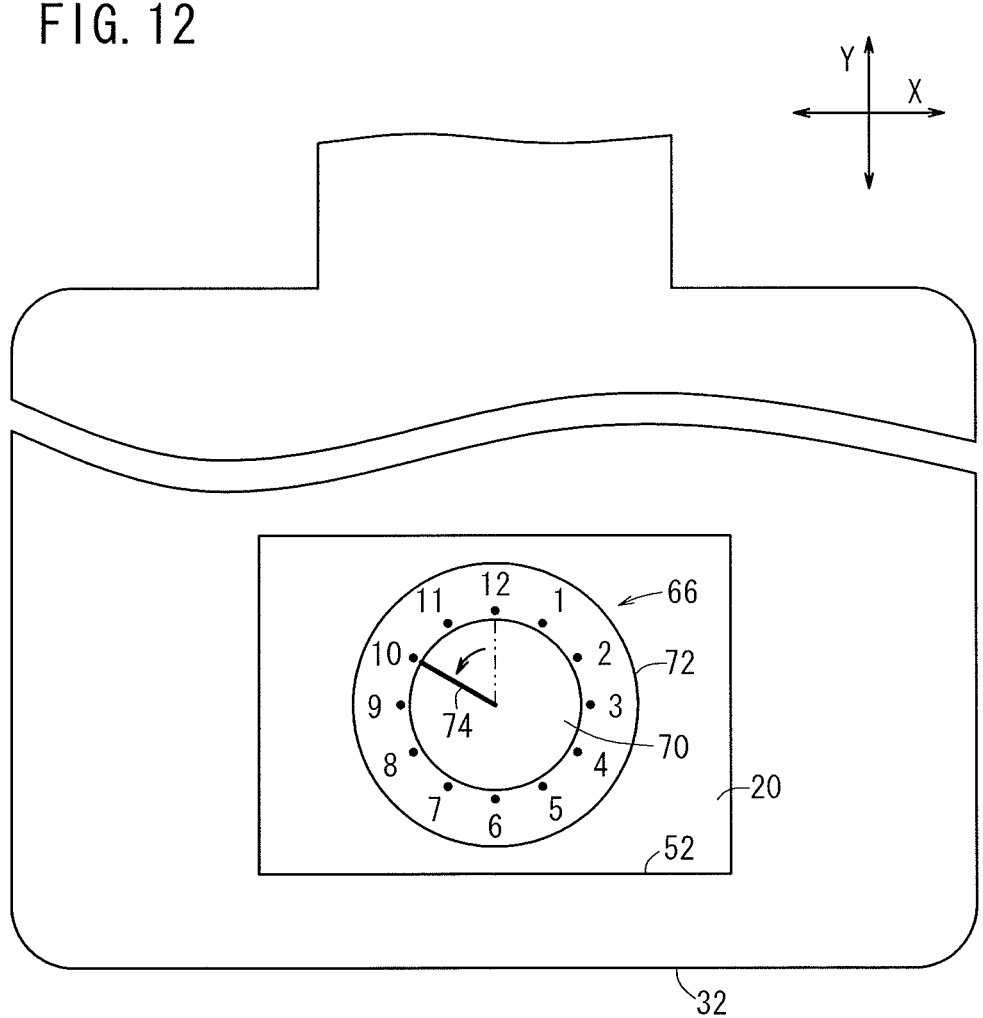
FIG. 12 is a plan view showing a dial adjusted based on the calculated result from an angle calculator.
Figure 13:
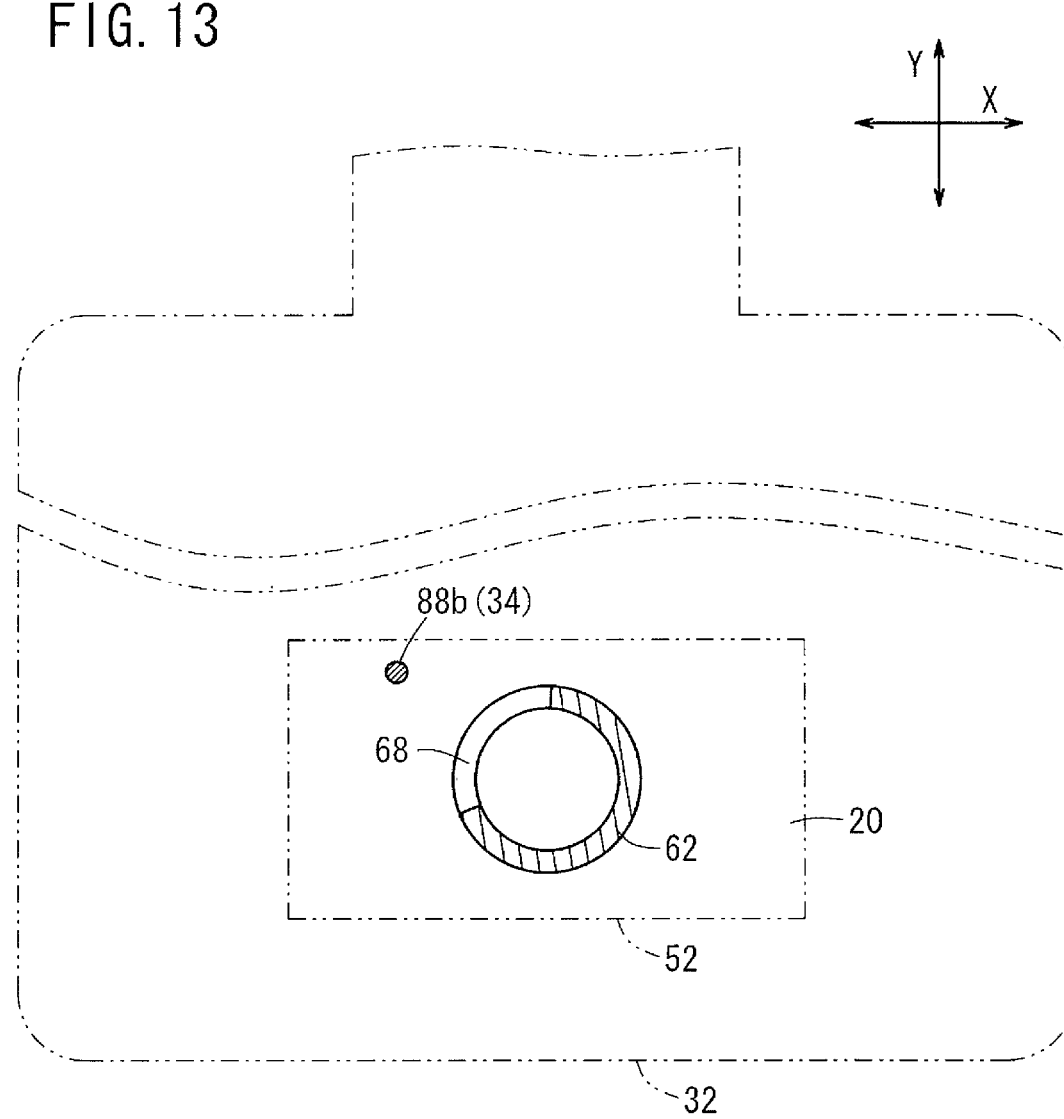
FIG. 13 is a cross-sectional view showing the position of the opening of the bioptic needle which corresponds to the adjusted dial.

As shown in FIG. 7, the console 38 is electrically connected to a display unit 78, an indicating unit 80, and an input unit 82. The display unit 78 displays two radiographic images (stereoscopic images) 84a, 84b; 86a, 86b (see FIGS. 10 and 11) which are acquired in stereoscopic image capturing processes.

In the present embodiment, before the bioptic needle 60 is inserted into the breast 20 compressed and secured by the compression plate 32 and the image capturing base 30, the radiation source 24 in the position A applies the radiation 22a to the breast 20, producing a first stereoscopic image 84a, and the radiation source 24 in the position B applies the radiation 22b to the breast 20, producing a first stereoscopic image 84b. While the bioptic needle 60 is being inserted in the breast 20, the radiation source 24 in the position A applies the radiation 22a to the breast 20, producing a second stereoscopic image 86a, and the radiation source 24 in the position B applies the radiation 22b to the breast 20, producing a second stereoscopic image 86b.

The indicating unit 80 comprises a pointing device such as a mouse or the like. When the technician or the like views the images (the first stereoscopic images 84a, 84b and the second stereoscopic images 86a, 86b) displayed on the display unit 78, the technician or the like can indicate a lesion (target, bioptic region 34) 88b (see FIG. 10) from which a tissue is to be sampled, among a plurality of lesions 88a through 88c in each of the first stereoscopic images 84a, 84b and each of the second stereoscopic images 86a, 86b, using the pointing device.

When the technician or the like views the images (the second stereoscopic images 86a, 86b) displayed on the display unit 78, the technician or the like can also indicate a feature point of the bioptic needle 60 in each of the second stereoscopic images 86a, 86b, using the indicating unit 80. If the display unit 78 comprises a touch-panel display unit, then the indicating unit 80 may be incorporated in the display unit 78.

According to the present embodiment, the pointed end N of the bioptic needle 60 is used as the feature point of the bioptic needle 60. Since the feature point of the bioptic needle 60 is set as one point, i.e., the pointed end N, the feature point of the bioptic needle 60 can accurately be indicated in each of the second stereoscopic images 86a, 86b. In the second stereoscopic images 86a, 86b, the pointed end N of the bioptic needle 60 is displayed without fail.

The input unit 82 comprises a keyboard, for example. The technician or the like can enter an inserting direction along which the bioptic needle 60 is to be inserted into the breast 20, and other data, using the input unit 82.

The console 38 includes a storage unit 90, a compression plate controller 92, an image capturing condition setting section 94, a radiation source controller 96, a detector controller 98, an image information storage unit 100, a CAD (Computer Aided Diagnosis) processor 102, a mode setting section 104, a bioptic region position calculator 106, a bioptic needle position calculator 108, a positional information storage unit 110, an opening position calculator 112, a decision section 114, a distance calculator 116, an angle calculator 118, and a bioptic needle controller 120.

The storage unit 90 stores first image capturing angle data, second image capturing angle data, first bioptic needle data, and second bioptic needle data.

The first image capturing angle data represent a title angle +θ1 (see FIG. 6) through which the radiation source 24 in the position A is tilted with respect to the central axis 76, and the second image capturing angle data represent a title angle −θ1 through which the radiation source 24 in the position B is tilted with respect to the central axis 76.

The first bioptic needle data represent an opening width L1 (see FIG. 3) of the opening 68 of the bioptic needle 60 in the directions indicated by the arrow Z, and the second bioptic needle data represent a distance L2 from the pointed end N of the tapered portion 64 of the bioptic needle 60 to an end of the opening 68 which is closer to the pointed end N.

The compression plate controller 92 serves to move the compression plate 32 in the directions indicated by the arrow Z. The image capturing condition setting section 94 sets image capturing conditions including a tube current and a tube voltage of the radiation source 24, an irradiation dosage and an irradiation time of the radiation 22, an image capturing method, and an imaging sequence. The radiation source controller 96 serves to energize the radiation source 24 according to the image capturing conditions.

The detector controller 98 controls the solid-state detector 28 to store radiographic images converted from the radiation 22 by the solid-state detector 28 into the image information storage unit 100. In the present embodiment, the detector controller 98 stores two radiographic images captured at two image capturing angles (stereoscopic angles) into the image information storage unit 100.

The CAD processor 102 processes the radiographic images stored in the image information storage unit 100, and displays the first stereoscopic images 84a, 84b and the second stereoscopic images 86a, 86b on the display unit 78 and/or the display control panel 40.

The mode setting section 104 sets a bioptic region indicating mode for indicating a bioptic region 34 in the first stereoscopic images 84a, 84b and the second stereoscopic images 86a, 86b and a bioptic needle indicating mode for indicating the pointed end N of the bioptic needle 60 in the second stereoscopic images 86a, 86b. The technician or the like can freely select the bioptic region indicating mode or the bioptic needle indicating mode from the mode setting section 104, using the indicating unit 80 for example. Therefore, the technician or the like can efficiently and accurately indicate the bioptic region 34 and the bioptic needle 60.

The bioptic region position calculator 106 calculates a three-dimensional coordinate (Xt, Yt, Zt) position of the bioptic region 34 (the central point T of the bioptic region 34) (hereinafter also referred to as "bioptic region coordinate position") in a three-dimensional coordinate system based on the information indicated by the indicating unit 80 in the bioptic region indicating mode, the first image capturing angle data, and the second image capturing angle data, stores the information of the calculated bioptic region coordinate position into the positional information storage unit 110, and outputs the information of the calculated bioptic region coordinate position to the bioptic needle controller 120.

The three-dimensional coordinate system has its origin (reference point) O that can be established as desired. In the present embodiment, the origin O is set on the central axis 76 at an intersection between the central axis 76 and an end face of the radiation source housing unit 26 which faces the compression plate 32 at the time the radiation source 24 is in the position C. In the three-dimensional coordinate system, the direction from the origin O toward the position A is used as a positive X-axis direction, the direction from the origin O toward the base 12 as a positive Y-axis direction, and the direction from the origin O toward the compression plate 32 as a positive Z-axis direction.

The bioptic needle position calculator 108 calculates a three-dimensional coordinate (Xn, Yn, Zn) position of the pointed end N of the bioptic needle 60 (hereinafter also referred to as "bioptic needle coordinate position") in the three-dimensional coordinate system based on the information indicated by the indicating unit 80 in the bioptic needle indicating mode, the first image capturing angle data, and the second image capturing angle data, stores the information of the calculated bioptic needle coordinate position into the positional information storage unit 110, and outputs the information of the calculated bioptic needle coordinate position to the opening position calculator 112.

The bioptic region coordinate position and the bioptic needle coordinate position may be calculated according to a known process of calculating a three-dimensional coordinate position in the stereoscopic image capturing process.

The opening position calculator 112 calculates a three-dimensional coordinate position of the opening 68 of the bioptic needle 60 based on the first bioptic needle data, the second bioptic needle data, the inserting direction inputted from the input unit 82, and the bioptic needle coordinate position, while the bioptic needle 60 is being inserted in the breast 20. Specifically, the opening position calculator 112 calculates a three-dimensional coordinate position of a central point H1 of one end of the wall that defines the opening 68, a three-dimensional coordinate position of a central point H2 of the opposite end of the wall that defines the opening 68, and outputs the calculated three-dimensional coordinate positions to the decision section 114. The three-dimensional coordinate positions of the central points H1, H2 are set as follows (see FIG. 3):

(1) Central point H1 (Xh, Yh, Zn-L1-L2)
(2) Central point H2 (Xh, Yh, Zn-L2)

The decision section 114 determines whether the bioptic region coordinate position is within the opening range of the opening 68 of the bioptic needle 60 in the directions indicated by the arrow Z or not while the bioptic needle 60 is being inserted in the breast 20. Specifically, the decision section 114 determines whether the central point T is positioned between the central points H1, H2 in terms of Z-axis coordinates or not. If the decision section 114 judges that the central point T is not positioned between the central points H1, H2, then the decision section 114 displays the decision on the display unit 78 and/or the display control panel 40.

The distance calculator 116 calculates a distance L (see FIG. 5) between the bioptic needle coordinate position and the bioptic region coordinate position, as projected onto an X-Y plane, and displays the calculated distance L on the display unit 78 and/or the display control panel 40.

The angle calculator (direction calculating means) 118 calculates a direction of the bioptic region coordinate position with respect to the bioptic needle coordinate position. Specifically, the angle calculator 118 calculates an angle β formed between a line segment D interconnecting the pointed end N of the bioptic needle 60 and the central point T of the bioptic region 34 and a reference line S extending from the axis Ax of the bioptic needle 60 toward the base 12 along a direction indicated by the arrow Y, and displays the calculated angle β on the display unit 78 and/or the display control panel 40.

The bioptic needle controller 120 moves the bioptic needle 60 to a given position through the bioptic hand assembly 36 based on the information of the bioptic region coordinate position which is output from the bioptic region position calculator 106.

A bioptic method using the mammographic system 10 thus constructed will be described below with reference to FIGS. 8 through 18.

Figure 8:
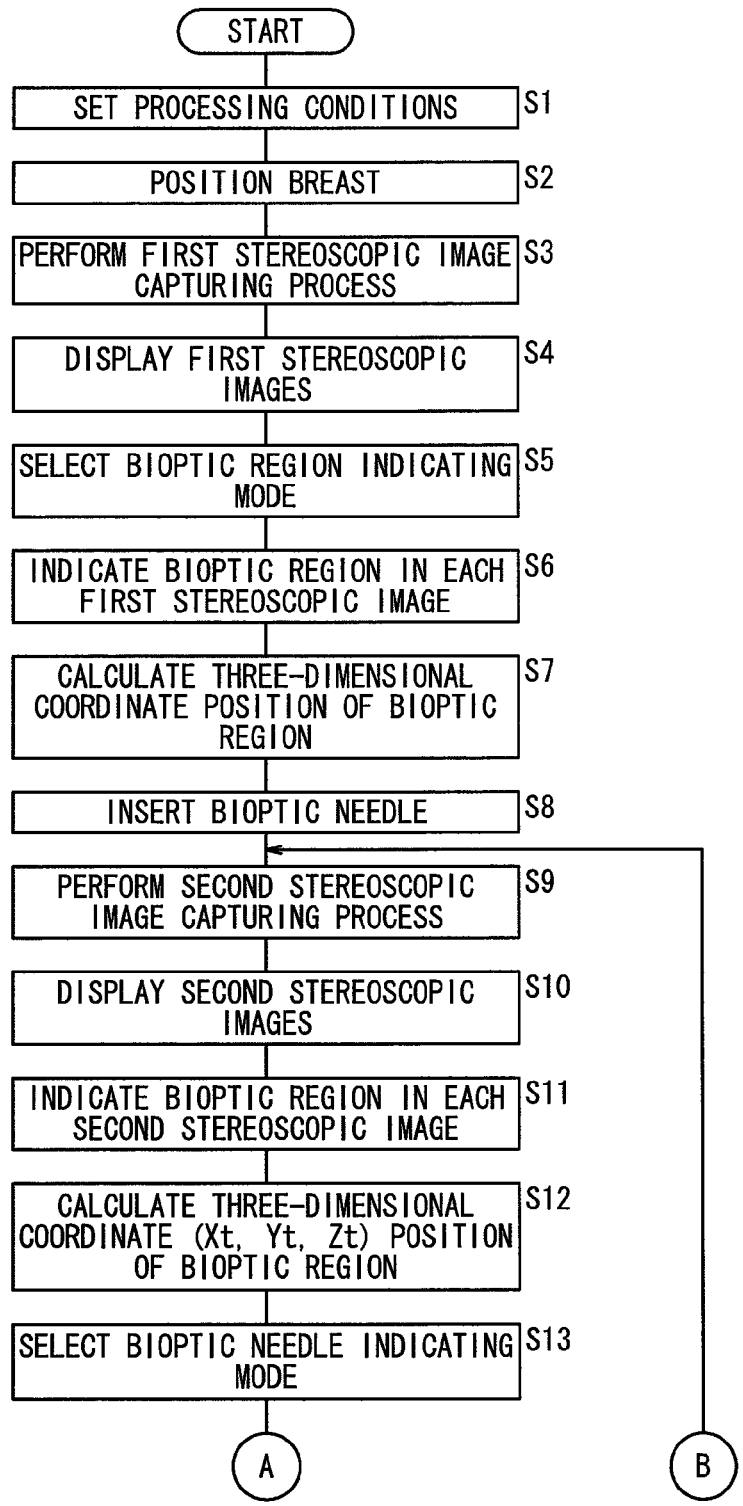
FIG. 8 is a flowchart of a bioptic method which is carried out using the mammographic system shown in FIG. 1, the flowchart including steps up to step S13.

First, the technician or the like sets image capturing conditions including a tube current and a tube voltage of the radiation source 24, an irradiation dosage and an irradiation time of the radiation 22, an image capturing method, and an imaging sequence depending on the breast 20, using image capturing condition setting section 94 (step S1 shown in FIG. 8). The image capturing conditions are set in the radiation source controller 96.

Then, the technician or the like positions the breast 20 of the examinee 18 (step S2). Specifically, the technician or the like places the breast 20 in a predetermined position on the image capturing base 30, i.e., a position facing the opening 52 in the compression plate 32, and then operates the compression plate controller 92 to move the compression plate 32 toward the image capturing base 30 in the direction indicated by the arrow Z, compressing and positioning the breast 20. The breast 20 is now compressed and secured in position by the image capturing base 30 and the compression plate 32.

Then, the radiation source controller 96 energizes the radiation source 24 to perform a first stereoscopic image capturing process on the breast 20 (step S3). Specifically, the radiation source housing unit 26 is turned about the hinge 42 to move the radiation source 24 successively to the positions A, B, from which the radiation source 24 applies respective radiations 22a, 22b to the breast 20. The radiations 22a, 22b which have passed through the breast 20 are detected by the solid-state detector 28 in the image capturing base 30, and converted into respective radiographic images by the solid-state detector 28.

The detector controller 98 controls the solid-state detector 28 to acquire the two radiographic images, and stores the two radiographic images into the image information storage unit 100.

Thereafter, the CAD processor 102 processes the two radiographic images stored in the image information storage unit 100 into first stereoscopic images 84a, 84b, and displays the first stereoscopic images 84a, 84b on the display unit 78 and/or the display control panel 40 (step S4). The first stereoscopic images 84a, 84b displayed on the display unit 78 will hereinafter be described below (see FIG. 10). Second stereoscopic images 86a, 86b will similarly be handled.

The technician or the like operates the indicating unit 80 to select the bioptic region indicating mode from the mode setting section 104 (step S5).

Then, while viewing the first stereoscopic images 84a, 84b, the technician or the like operates the indicating unit 80 to indicate a lesion (bioptic region 34) 88b from which a tissue is to be sampled, among a plurality of lesions 88a through 88c in each of the first stereoscopic images 84a, 84b (step S6).

When the bioptic region 34 is indicated in each of the first stereoscopic images 84a, 84b, the bioptic region position calculator 106 calculates a three-dimensional coordinate position of the bioptic region 34 indicated in each of the first stereoscopic images 84a, 84b (step S7).

Then, the technician or the like determines an inserting direction along which the bioptic needle 60 is to be inserted, from the first stereoscopic images 84a, 84b, and inputs the determined inserting direction using the input unit 82. In the present embodiment, the inserting direction of the bioptic needle 60 is a direction indicated by the arrow Z.

Then, the bioptic needle controller 120 moves the bioptic needle 60 based on the information of the bioptic region coordinate information from the bioptic region position calculator 106 to insert the bioptic needle 60 into the breast 20 (step S8). Specifically, the bioptic needle controller 120 moves the first arm 56 and the second arm 58 of the bioptic hand assembly 36 in the X-Y plane until the bioptic needle 60 is placed in a position confronting the bioptic region 34, i.e., a position confronting the bioptic region 34 along the directions indicated by the arrow Z, and thereafter moves the bioptic needle 60 toward the image capturing base 30.

Thereafter, the radiation source controller 96 energizes the radiation source 24 to perform a second stereoscopic image capturing process on the breast 20 which is being pierced with the bioptic needle 60 (step S9). Step S9 is identical to step S3 and will not be described in detail below. Other subsequent steps which are identical to those described above will not be described in detail below.

The radiographic images detected by the solid-state detector 28 are stored into the image information storage unit 100. After the radiographic images stored in the image information storage unit 100 are processed by the CAD processor 102, they are displayed as second stereoscopic images 86a, 86b on the display unit 78 (step S10, see FIG. 11).

Then, while viewing the second stereoscopic images 86a, 86b, the technician or the like operates the indicating unit 80 to indicate a bioptic region 34 in each of the second stereoscopic images 86a, 86b (step S11).

When the bioptic region 34 is indicated in each of the second stereoscopic images 86a, 86b, the bioptic region position calculator 106 calculates a three-dimensional coordinate (Xt, Yt, Zt) position of the bioptic region 34 indicated in each of the second stereoscopic images 86a, 86b (step S12).

Then, the technician or the like operates the indicating unit 80 to select the bioptic needle indicating mode from the mode setting section 104 (step S13).

Figure 9:
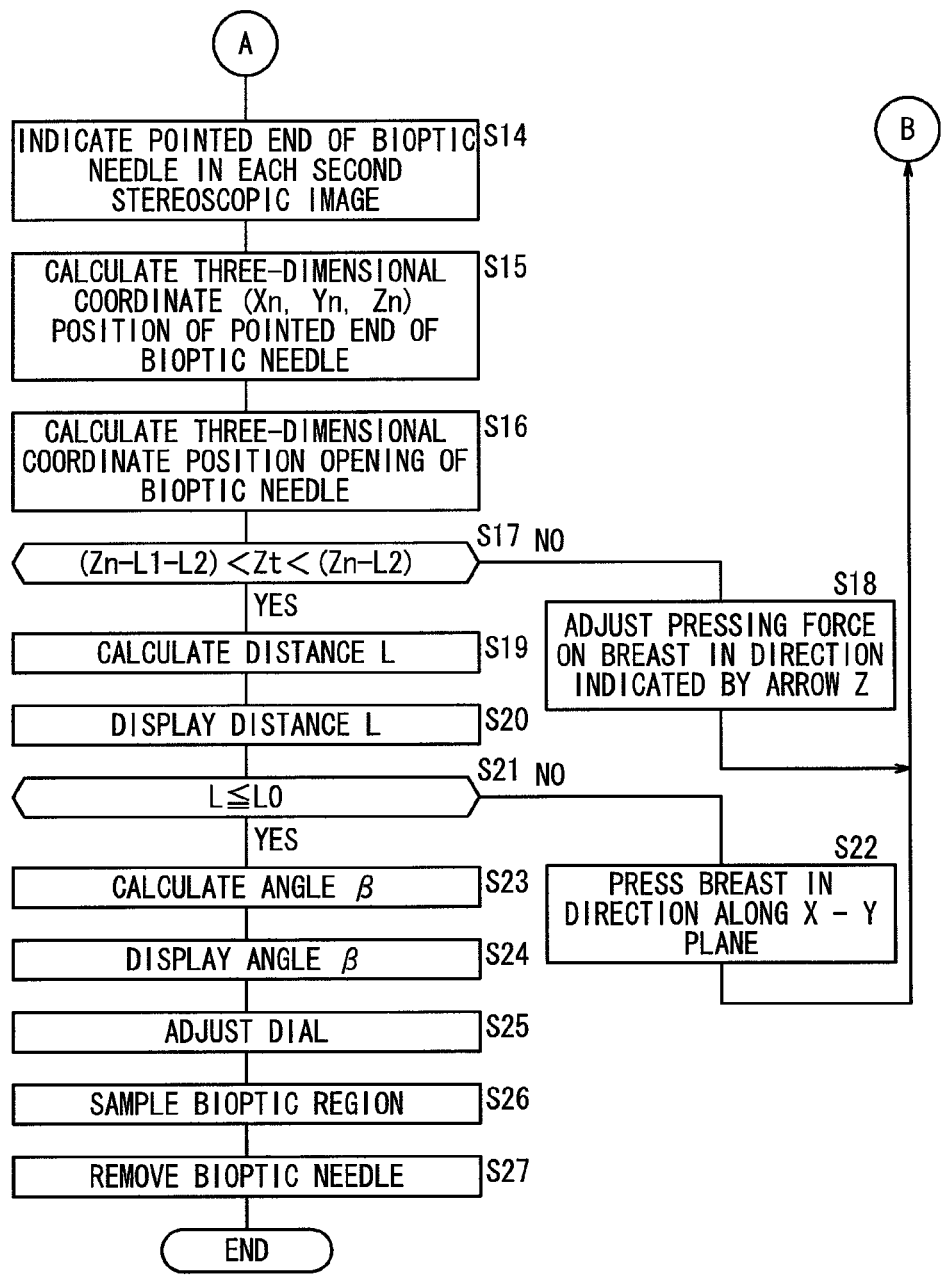
FIG. 9 is a flowchart of the bioptic method which is carried out using the mammographic system shown in FIG. 1, the flowchart including steps from step S14.

Then, while viewing the second stereoscopic images 86a, 86b, the technician or the like operates the indicating unit 80 to indicate the pointed end N of the bioptic needle 60 in each of the second stereoscopic images 86a, 86b (step S14 shown in FIG. 9).

When the pointed end N of the bioptic needle 60 is indicated in each of the second stereoscopic images 86a, 86b, the bioptic needle position calculator 108 calculates a three-dimensional coordinate (Xn, Yn, Zn) position of the bioptic needle 60 indicated in each of the second stereoscopic images 86a, 86b (step S15).

Subsequently, the opening position calculator 112 calculates a three-dimensional coordinate position (central points H1, H2) of the opening 68 of the bioptic needle 60 (step S16). Specifically, the opening position calculator 112 calculates the three-dimensional coordinate position based on the first bioptic needle data, the second bioptic needle data, the inserting direction, and the bioptic needle coordinate position.

Then, the decision section 114 determines whether the bioptic region coordinate position is within the opening range of the opening 68 of the bioptic needle 60 in the directions indicated by the arrow Z or not (step S17). Specifically, the decision section 114 determines whether the Z-axis bioptic region coordinate (Zt) is greater than the Z-axis coordinate of the central point H1 (Zn-L1-L2) and smaller than the Z-axis coordinate of the central point H2 (Zn-L2) or not.

If the answer is NO in step S17, the compression plate controller 92 moves the compression plate 32 in the directions indicated by the arrow Z to adjust the pressing force applied to the breast 20 in the directions indicated by the arrow Z (step S18). Since the position of the bioptic region 34 in the directions indicated by the arrow Z is now finely adjusted, the bioptic region 34 can be positioned in the opening range of the opening 68 of the bioptic needle 60 in the directions indicated by the arrow Z. Then, control goes back to step S9 shown in FIG. 8.

If the answer is YES in step S17, then the distance calculator 116 calculates a distance L between the bioptic needle coordinate position and the bioptic region coordinate position in the X-Y plane, and displays the calculated distance L on the display unit 78 (step S20). The distance L can be calculated according to the following equation (1):

$$L=\{(Xn-Xt)^2+(Yn-Yt)^2\}^{1/2} \quad (1)$$

Thereafter, the technician or the like determines whether or not the calculated distance L is equal to or smaller than a reference distance L0 (step S21). The reference distance L0 may be a distance along which a tissue can be sampled from the bioptic region 34 under suction, for example, and is determined depending on the type of the bioptic needle 60.

If the technician or the like decides that the distance L is greater than the reference distance L0 in step S21, then the technician or the like presses the breast 20 in a direction parallel to the X-Y plane (step S22). Since the position of the breast 20 in a direction parallel to the X-Y plane can be finely adjusted, the distance L between the bioptic needle coordinate position and the bioptic region coordinate position can be made smaller than the reference distance L0. Thereafter, control goes back to step S9 shown in FIG. 8.

If the technician or the like decides that the distance L is equal to or smaller than the reference distance L0 in step S21, then the angle calculator 118 calculates an angle β formed between the reference line S and the line segment D (step S23), and displays the calculated angle β on the display unit 78 (step S24). The angle β can be calculated according to the following equation (2):

$$\beta=\arctan\{(Xn-Xt)/(Yt-Yn)\} \quad (2)$$

Then, the technician or the like adjusts the dial 70 based on the calculated angle β. If the angle β is 60 degrees, then the technician or the like turns the dial 70 counterclockwise through 60 degrees (see FIG. 12). As a result, the opening 68 is oriented in a 10 o'clock direction, facing the bioptic region 34 (see FIG. 13). Stated otherwise, a line passing through the axis Ax of the bioptic needle 60 and the center H0 of the opening 68 passes through the central point T of the bioptic region 34 in the X-Y plane.

Thereafter, the bioptic needle 60 starts to sample a tissue from the bioptic region 34 under suction (step S26). The bioptic needle 60 is then moved toward the compression plate 32 until it is removed from the breast 20 (step S27). The bioptic method is now ended.

In the present embodiment, the opening 68 of the bioptic needle 60 can be brought into facing relationship to the bioptic region 34 when the dial 70 is adjusted based on the angle β calculated by the angle calculator 118. Therefore, the bioptic needle 60 can reliably sample a tissue from the bioptic region 34. According to the present embodiment, the process of calculating the angle β is not complex because there is no need to generate a three-dimensional image.

In step S16, the three-dimensional coordinate positions of the central points H1, H2 of the opening 68 of the bioptic needle 60 are calculated based on the first bioptic needle data, the second bioptic needle data, the inserting direction, and the bioptic needle coordinate position. Consequently, it is easy to determine whether the bioptic region coordinate position is in the opening range of the opening 68 in the directions indicated by the arrow Z.

In the present embodiment, furthermore, the decision made by the decision section 114, the distance L calculated by the distance calculator 116, and the angle φ calculated by the angle calculator 118 are displayed on the display unit 78. Therefore, the display unit 78 functions as an announcing means. The mammographic system 10 is thus made up of a smaller number of parts than if an announcing means is provided separately from the display unit 78. However, the mammographic system 10 may include an announcing means for announcing the decision made by the decision section 114 with audible sounds or the like, etc. in addition to the display unit 78.

Figure 14:
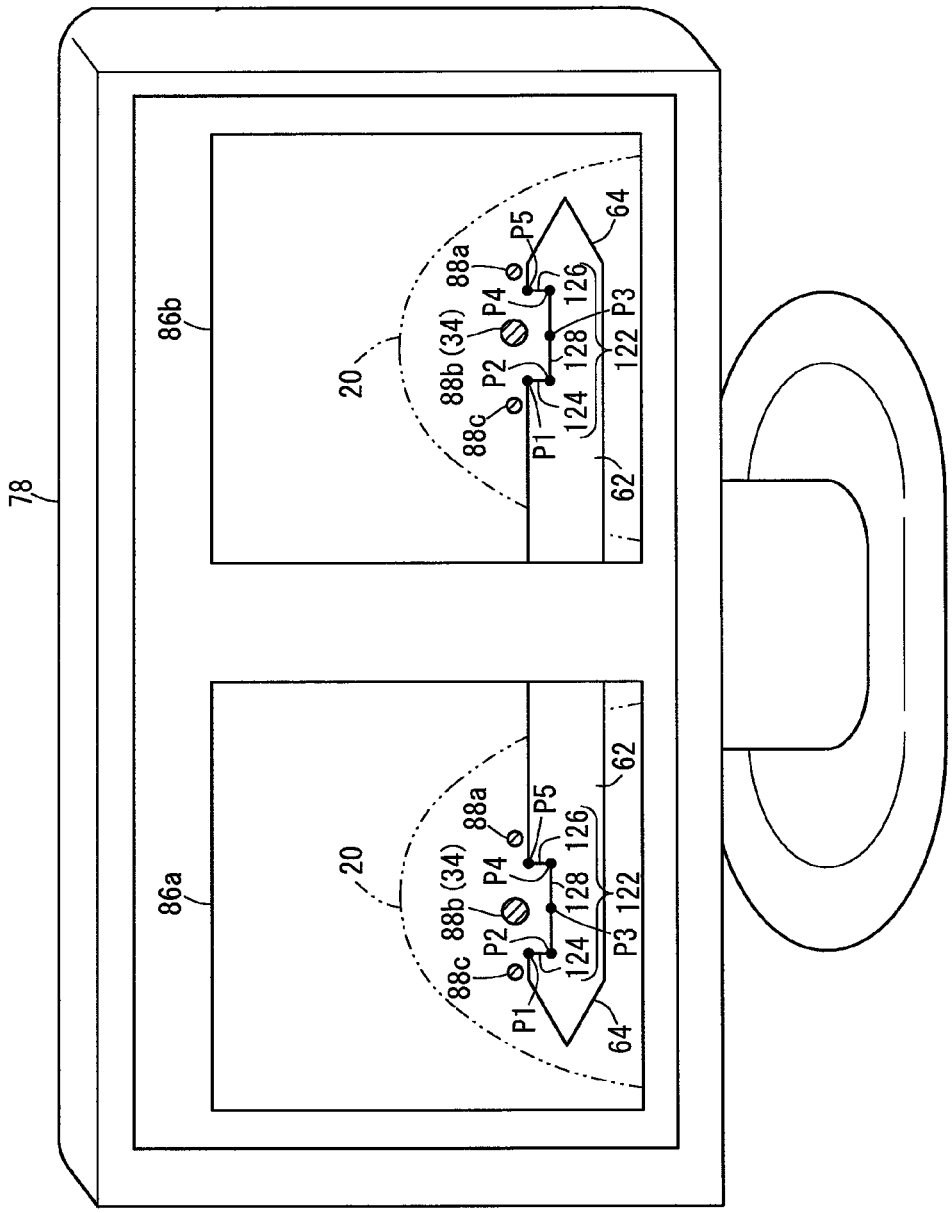
FIG. 14 is a perspective view showing another feature point of the bioptic needle.

In the present embodiment, the bioptic needle 60 may have a feature point that is selected as desired. For example, as shown in FIG. 14, the bioptic needle 60 may have a feature point that is positioned on an opening forming line 122 which defines the opening 68 of the bioptic needle 60 displayed in each of the second stereoscopic images 86a, 86b. The bioptic needle position calculator 108 can easily calculate a three-dimensional coordinate position of the opening 68 of the bioptic needle 60. The opening forming line 122, which is substantially U-shaped (channel-shaped), includes a pair of opposite sides 124, 126 which face each other and a joining side 124 interconnecting the opposite sides 124, 126. The expression "substantially U-shaped" used above means that the opening forming line 122 has a U-shape or a shape similar to a U-shape.

Specifically, the bioptic needle 60 should preferably have a feature point which is either one of points P1 through P5 shown in FIG. 14. In FIG. 14, the point P1 is positioned at an end of the opposite side 124, the point P2 at the intersection between the opposite side 124 and the joining side 128, the point P3 at the center of the joining side 128, the point P4 at the intersection between the opposite side 126 and joining side 128, and the point P5 at an end of the opposite side 126.

With either one of the points P1 through P5 being selected as the feature point of the bioptic needle 60, the bioptic needle position calculator 108 can easily calculate a three-dimensional coordinate position of the opening 68 of the bioptic needle 60, and the feature point of the bioptic needle 60 is indicated with increased accuracy in each of the second stereoscopic images 86a, 86b.

The radiographic image capturing system may perform a tomosynthetic image capturing process, and may use preferable two of a plurality of tomosynthetic images as stereoscopic images.

Although certain preferred embodiments of the present invention have been shown and described in detail, it should be understood that various changes and modifications may be made therein without departing from the scope of the appended claims.

What is claimed is:

1. A radiographic image capturing system comprising:
   a bioptic needle to be inserted into an object to be examined for sampling a tissue from a bioptic region of the object through an opening of the bioptic needle;
   a display configured to display stereoscopic images acquired by applying a radiation to the object while the bioptic needle is being inserted in the object;
   a console connected to the display; and
   a pointing device indicating at least a first indicating signal displayed on the display indicating a feature point of the bioptic needle in each of the stereoscopic images displayed on the display and a second indication signal displayed on the display indicating the bioptic region in each of the stereoscopic images displayed on the display unit, said first and second indicating signals being input by a user;
   wherein the console includes:
   a bioptic needle position calculator configured to calculate a three-dimensional coordinate position of the feature point of the bioptic needle, based on the first indication signal;
   a bioptic region position calculator configured to calculate a three-dimensional coordinate position of the bioptic region, based on the second indication signal;
   a direction processor configured to calculate a direction of the three-dimensional coordinate position of the bioptic region with respect to the three-dimensional coordinate position of the feature point of the bioptic needle, based on the three-dimensional coordinate position of the feature point of the bioptic needle calculated by the bioptic needle position calculator and the three-dimensional coordinate position of the bioptic region calculated by the bioptic region position calculator; and
   an output device comprising at least one of an audible device and the display, configured to announce the direction calculated by the direction calculator.

2. The radiographic image capturing system according to claim 1, wherein the console further comprises:
   a distance calculator configured to calculate a distance represented by the length of a line segment which interconnects the three-dimensional coordinate position of the feature point of the bioptic needle and the three-dimensional coordinate position of the bioptic region, as projected onto a plane lying perpendicularly to an inserting direction along which the bioptic needle is inserted in the object;
   wherein the output device announces the distance calculated by the distance calculator.

3. The radiographic image capturing system according to claim 2, wherein the console further comprises:
   a decision processor configured to determine whether the three-dimensional coordinate position of the bioptic region is within an opening range of the opening of the bioptic needle or not in the inserting direction, based on an operation request from the user;
   wherein the output device announces a decision made by the decision processor if the decision processor judges that the three-dimensional coordinate position of the bioptic region falls outside of the opening range.

4. The radiographic image capturing system according to claim 3, wherein the console further comprises an opening position calculator configured to calculate a position of the opening of the bioptic needle based on the three-dimensional coordinate position of the feature point of the bioptic needle.

5. The radiographic image capturing system according to claim 4, further comprising a user interface configured to receive an input of a third indication signal representing the inserting direction along which the bioptic needle is inserted in the object,
   wherein the opening position calculator calculates the position of the opening of the bioptic needle based on the third indication signal.

6. The radiographic image capturing system according to claim 3, further comprising a display driver configured to control the display to display the direction calculated by the direction calculator, the distance calculated by the distance calculator, and the decision made by the decision processor.

7. The radiographic image capturing system according to claim 1, wherein the console further comprises a mode setting processor setting a bioptic needle indicating mode for inputting the first indication signal and a bioptic region indicating mode for inputting the second indication signal.

8. A bioptic method inserting a bioptic needle into an object to be examined and sampling a tissue from a bioptic region of the object through an opening of the bioptic needle, comprising:
   a displaying step of operating a console to display on a display stereoscopic images acquired by applying a radiation to the object while the bioptic needle is being inserted in the object;
   a first indication signal inputting step of operating a pointing device to input a first indication signal on the display indicating a feature point of the bioptic needle in each of the stereoscopic images displayed on the display, said first indication signal provided by user input;
   a second indication signal inputting step of operating the pointing device to input, based on an operation request from a user, a second indication signal on the display indicating the bioptic region in each of the stereoscopic images displayed on the display said second indication signal provided by user input;
   a bioptic needle position calculating step of calculating, with a bioptic needle position calculator, a three-dimensional coordinate position of the feature point of the bioptic needle based on the first indication signal;
   a bioptic region position calculating step of calculating, with a bioptic region position calculator, a three-dimensional coordinate position of the bioptic region based on the second indication signal;
   a direction calculating step of calculating, with a direction calculator, a direction of the three-dimensional coordinate position of the bioptic region with respect to the three-dimensional coordinate position of the feature point of the bioptic needle, based on the three-dimensional coordinate position of the feature point of the bioptic needle calculated in the bioptic needle position calculating step and the three-dimensional coordinate position of the bioptic region calculated in the bioptic region position calculating step; and
   an announcing step of announcing, with an output device comprising at least one of an audible device and the display, the direction calculated in the direction calculating step.

* * * * *